United States Patent
Levine et al.

(10) Patent No.: US 7,235,073 B2
(45) Date of Patent: Jun. 26, 2007

(54) COOLED ELECTROSURGICAL FORCEPS

(75) Inventors: Andy Levine, Newton Center, MA (US); John Meade, Mendon, MA (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 09/886,658

(22) Filed: Jun. 21, 2001

(65) Prior Publication Data

US 2002/0016591 A1 Feb. 7, 2002

Related U.S. Application Data

(60) Provisional application No. 60/216,245, filed on Jul. 6, 2000.

(51) Int. Cl.
*A61B 18/18* (2006.01)

(52) U.S. Cl. ............................ 606/48; 606/51; 606/52; 606/27; 606/25

(58) Field of Classification Search ............. 606/46–52, 606/36–45; 600/372, 373, 374
See application file for complete search history.

(56) References Cited

U.S. PATENT DOCUMENTS

| | | | |
|---|---|---|---|
| 3,496,942 A | 2/1970 | Shipley | 128/401 |
| 3,929,136 A | 12/1975 | Kreeb et al. | 128/303.1 |
| 3,991,764 A | 11/1976 | Incropera et al. | 128/303.1 |
| 4,074,718 A | 2/1978 | Morrison, Jr. | 128/303.14 |
| 4,202,336 A | 5/1980 | van Gerven | 128/303.1 |
| 4,492,231 A | 1/1985 | Auth | 128/303.17 |
| 4,532,924 A | 8/1985 | Auth et al. | 128/303.17 |
| 4,674,499 A | 6/1987 | Pao | 128/303.14 |
| 4,686,980 A * | 8/1987 | Williams et al. | 606/48 |
| 4,931,047 A | 6/1990 | Broadwin et al. | 604/22 |
| 5,171,311 A | 12/1992 | Rydell et al. | 606/48 |
| 5,197,963 A | 3/1993 | Parins | 606/46 |
| 5,230,349 A | 7/1993 | Langberg | 128/786 |
| 5,234,004 A | 8/1993 | Hascoet et al. | 607/116 |
| 5,282,799 A | 2/1994 | Rydell | 606/48 |
| 5,318,589 A | 6/1994 | Lichtman | 606/205 |
| 5,334,193 A | 8/1994 | Nardella | 606/41 |

(Continued)

FOREIGN PATENT DOCUMENTS

| | | |
|---|---|---|
| AU | 120788 | 1/1946 |
| EP | 0 246 350 | 5/1986 |
| EP | 0480639 A2 | 4/1992 |
| EP | 0 761 174 | 3/1997 |
| WO | WO 98/53750 | 12/1998 |
| WO | WO 01/15615 A1 | 3/2001 |

OTHER PUBLICATIONS

Brochure on Seitzinger Tripolar™ Cutting Forceps, Cabot Technology Corp., 1994, consisting of three pages.
Holman, J.P., *Heat Transfer*, Fourth Edition, McGraw–Hill Book Company, pp. 464–467.
Hoffmann, E., et al., "Temperature-controlled radiofrequency catheter ablation of AV conduction: first clinical experience," *European Heart Journal*, 14:57–64, (1993).
Bart, S.F., et al., "The Mechanism of Electrosurgical Coagulation: Steam Evolution Versus Dielectric Breakdown," *IEEE*, pp. 297–300, (1985).
Neiman, T.S., et al., "Thermal Characterization of Electrosurgery," *Biomat., Med. Dev., Art. Org.*, 11(1):93–101, (1983).

*Primary Examiner*—Roy D. Gibson
*Assistant Examiner*—Peter J Vrettakos
(74) *Attorney, Agent, or Firm*—Verne E. Kreger, Jr.

(57) ABSTRACT

Bipolar electrosurgical forceps includes a first electrode attached to a first heat pipe and a second electrode attached to a second heat pipe. The heat pipe can be removably attached to the forceps. The forceps can also include a securing mechanism that secures the removable heat pipes to the device.

20 Claims, 6 Drawing Sheets

U.S. PATENT DOCUMENTS

| | | | |
|---|---|---|---|
| 5,342,357 A | 8/1994 | Nardella | 606/40 |
| 5,348,554 A | 9/1994 | Imran et al. | 606/41 |
| 5,417,686 A | 5/1995 | Peterson et al. | 606/25 |
| 5,437,662 A | 8/1995 | Nardella | 606/40 |
| 5,478,351 A | 12/1995 | Meade et al. | 606/205 |
| 5,499,992 A | 3/1996 | Meade et al. | 606/170 |
| 5,647,871 A | 7/1997 | Levine et al. | 606/45 |
| 5,885,280 A | 3/1999 | Nettekoven et al. | 606/41 |
| 5,925,039 A | 7/1999 | Landingham | 606/41 |
| 6,056,747 A | 5/2000 | Saadat et al. | 606/50 |
| 6,074,389 A * | 6/2000 | Levine et al. | 606/45 |
| 6,090,107 A | 7/2000 | Borgmeier et al. | 606/41 |
| 6,206,876 B1 | 3/2001 | Levine et al. | 606/45 |
| 6,293,946 B1 * | 9/2001 | Thorne | 606/48 |

* cited by examiner

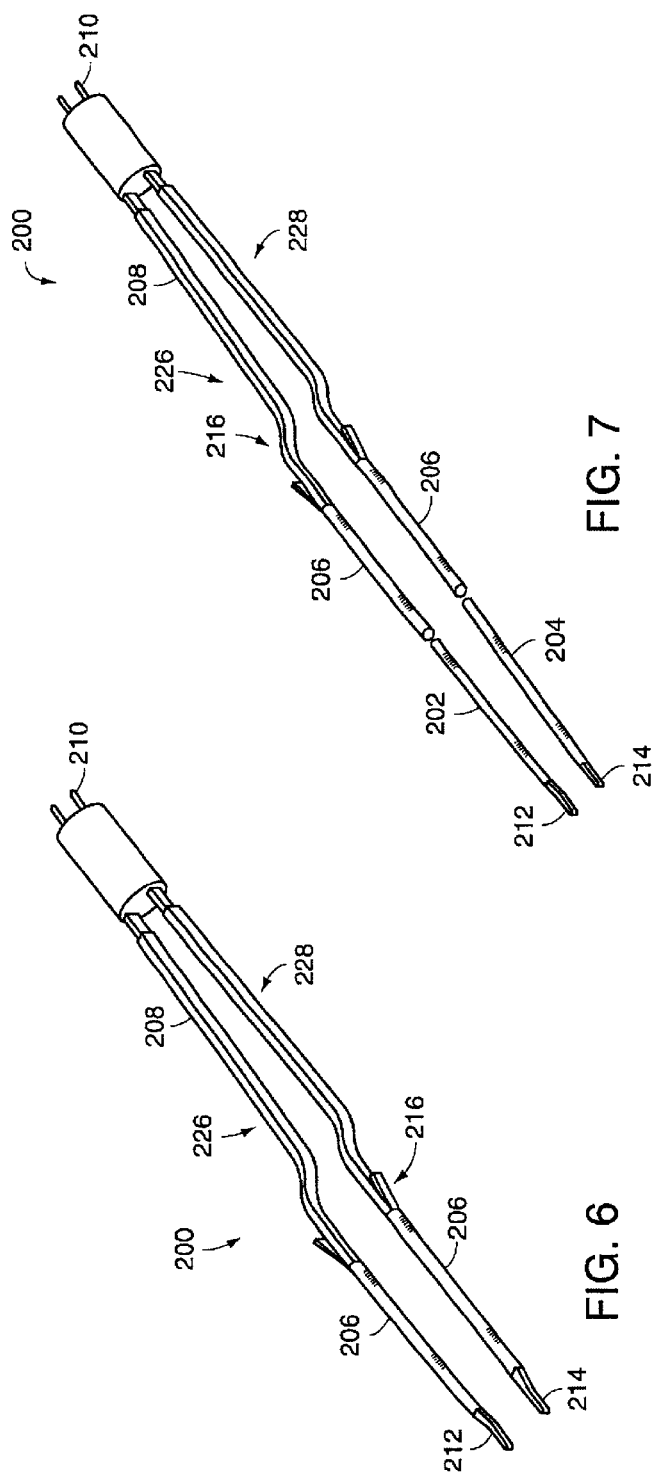

COOLED ELECTROSURGICAL FORCEPS

RELATED APPLICATION(S)

This application claims the benefit of U.S. Provisional Application No. 60/216,245, filed on Jul. 6, 2000. The entire teachings of the above application is incorporated herein by reference.

BACKGROUND OF THE INVENTION

Electrosurgery is commonly used to cauterize, cut and/or coagulate tissue. In typical electrosurgical devices, RF electrical energy is applied to the tissue being treated. Local heating of the tissue occurs, and, depending upon the waveform of the applied energy and the electrode geometry, the desired effect is achieved. By varying the power output and the type of electrical waveform, it is possible to control the extent of heating and, thus, the resulting surgical effect. For example, a continuous sinusoidal waveform is best suited for cutting, while a waveform having periodically spaced bursts of a partially rectified signal produces coagulation.

In bipolar electrosurgery, the electrosurgical device includes two electrodes. The tissue being treated is placed between the electrodes, and the electrical energy is applied across the electrodes. In monopolar electrosurgery, the electrical excitation energy is applied to a single electrode at the surgical site, and a grounding pad is placed in contact with the patient. The energy passes from the single monopolar electrode through the tissue to the grounding pad.

Bipolar electrosurgical devices are generally known to be safer than monopolar electrosurgical devices because the area of tissue through which electrical current passes is confined to the area close to the two electrodes of the bipolar device. However, bipolar devices include several drawbacks. For example, bipolar devices tend to char tissue during use and develops an open circuit relatively quickly because the electrical energy delivered by the devices is concentrated at the tissue located between the two electrodes. Bipolar devices also tend to adhere or stick to tissue during use. Any sticking of tissue to one or both electrodes short circuits the electrical energy and reduces the effectiveness of the device on the desired target tissues. To minimize tissue sticking, power settings on a bipolar generator are typically decreased compared to the settings on monopolar generator outputs. While this reduces charring and sticking, it also slows the intended effect of cauterization and makes the cutting of tissue with bipolar energy impractically slow, thereby slowing the progress of a surgery. For this reason, bipolar instruments have not been readily accepted by general surgeons in spite of their safety advantages.

Improving the effectiveness of bipolar electrosurgical devices includes eliminating the sticking of target tissues to the electrodes and reducing the formation of char material. Such improvements reduce short circuiting of the electrodes during operation and allow the electrodes to be passed from one target to another without the need for cleaning. The use of devices having heat pipes that conduct heat from the electrode and a surgical site to a heat exchanger, such as are disclosed in U.S. Pat. No. 6,074,389, herein incorporated by reference in its entirety, can be used to overcome these shortcomings. Such electrosurgical devices permit the user to increase the power levels of an attached electrosurgical generator during a surgical procedure. This speeds the action of the instruments compared to other currently available bipolar instruments.

SUMMARY OF THE INVENTION

Electrosurgery forceps include an electrical connector and a pair of flexible tines attached to the connector. The forceps also include electrodes at the end of each tine and a heat pipe within each tine to dissipate heat from the electrodes.

The electrodes can be formed of a material having a thermal conductivity between 375 W/m¯K and 420 W/m¯K, such as copper or silver. The electrodes can be attached to the heat pipes, such as by soldering, or can be formed integrally with the heat pipes. The heat pipes can include a curvature relative to the long axis of the heat pipes to aid in alignment of the electrodes material can surround an outer portion of the forceps.

The heat pipes can be removably attached to the tines. The tines can include heat pipe mounts such that the heat pipes slidably attach to the heat pipe mounts. The heat pipe mounts can also include a curved geometry relative to a long axis of the tines to adjust the curvature of the heat pipes. The forceps can also include a securing mechanism that secures the heat pipes to the tines.

The tines can include a grasping portion. The grasping portion can include an offset that allows the forceps to be used at a surgical site while providing a clear view of the surgical site by a user. The heat pipes can also include proximal portions that extend to the offset of the grasping portion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6 and 7 illustrate bipolar surgical forceps having detachable heat pipes, shown in a connected and unconnected state, respectively.

DETAILED DESCRIPTION OF THE INVENTION

A description of preferred embodiments of the invention follows.

In order to minimize or eliminate sticking of a bipolar electrosurgical device to tissue, the temperature of the electrodes is maintained below the temperature at which proteins denature and cause tissue to stick to metals. This temperature is approximately 80° C. and is described in detail in U.S. Pat. No. 5,647,871, herein incorporated by reference in its entirety. Most electrosurgical instruments are made of stainless steel or nickel because stainless steel and nickel are well known, biocompatible materials that tend to have stronger mechanical properties than the more thermally conductive materials. However, the thermal conductivity of stainless steel and nickel is relatively low (20–70 W/m¯K). To maintain the tips of bipolar instruments below 80° C., the electrodes can be fabricated from high thermal conductivity materials, such as copper or silver (375–420 W/m¯), for example.

Connecting the tips or electrodes of the electrosurgical instruments to a high thermal conductivity device, such as a heat pipe (10–20 times the thermal conductivity of copper) can also maintain the tips of the electrosurgery device below 80° C. The use of a heat pipe is described in U.S. Pat. No. 6,074,389, herein incorporated by reference in its entirety.

The heat pipe includes a sealed internal cavity that is partially evacuated and contains a heat transfer fluid, such as water. An outer shell can be made of a conductive metallic material, such as copper. During operation, electrical energy is conducted along the conductive outer shell of the heat pipe to the distal end. The heat pipe is able to transfer the heat conducted from the tissue to the electrodes of the instrument back to the handle of the instrument with a very small temperature rise. The heat can be released to the walls of the heat pipe or to heat transfer fins and a heat sink located in the handle. Natural convection and radiation are used to dissipate the heat to the atmosphere.

Because copper may oxidize, the tips or electrodes of the bipolar electrosurgical instruments are preferably coated with high thermally conductive, biocompatible coatings such as nickel and gold.

The amount of heat that the instruments must transfer from the tissue is variable, depending on the geometry of the electrosurgery tip and the power applied from the generator. For example, calculations and testing on electrosurgery devices showed that while applying up to 80 watts of energy to tissue with a 50% duty cycle at the tip of a 3 mm heat pipe, only 1–2 watts of energy needed to be transferred from the tip of the device to maintain a low temperature. Most of the energy transferred into the tissue is used to boil the water located in the tissue. Much of the energy is also carried away into the tissue by conduction and blood flow.

Figure 1:
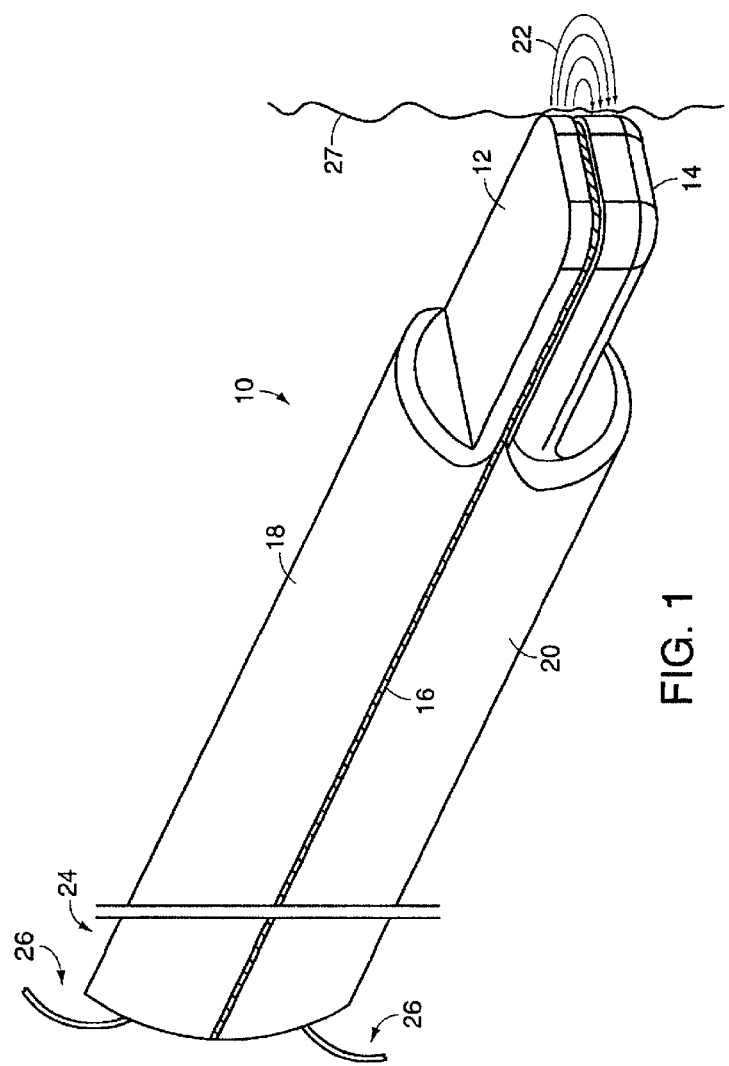
FIG. 1 illustrates a schematic representation of a bipolar electrosurgical device.

FIG. 1 illustrates, generally, a bipolar electrosurgical device, given as 10. The device 10 includes a first electrode 12 and a second electrode 14 attached to a first heat pipe 18 and a second heat pipe 20, respectively. The heat pipes 18, 20 and electrodes 12, 14 are separated by an electrically insulating material 16 that helps to maintain separate electrical paths between the first electrode 12 and first heat pipe 18 and the second electrode 14 and second heat pipe 20. The insulating material 16 can be a ceramic material, such as alumina ceramic, and can have a thickness between 0.010 inches and 0.030 inches.

The proximal ends 24 of the heat pipes 18, 20 include electrical wire leads 26 that attach to the bipolar output of an RF electrosurgical generator. The heat pipes 18, 20 conduct electrical energy from the generator to the electrodes 12, 14. The first electrode 12 has a first polarity and the second electrode 14 has a second polarity. When the device 10 is brought into contact with a tissue 27, energy 22 from the first electrode 12 travels through the tissue 27 toward the second electrode 14, thereby coagulating the tissue 27. The energy 22 can be transferred by a current flow between the electrodes 12, 14. For example, when the first electrode 12 includes a positive polarity and the second electrode 14 includes a negative polarity, energy 22 travels from the first electrode 12 toward the second electrode 14. The energy can also be microwave energy from a microwave source.

The amount of heat that the heat pipes 18, 20 transfer is small compared to the amount of electrical power delivered to the tissue. This is because most of the power delivered to the tissue is dissipated by the blood flow in the tissue and by the creation of steam from the tissue. For a power setting of 50 watts, approximately 1–2 watts are transferred by the heat pipes 18, 20 to maintain the tip at 80° C. With a relatively small amount of power transferred, the size of the heat pipes 18, 20 can be minimized. Currently, heat pipes are available having diameter of 2 or 3 mm, such as manufactured by Thermacore (780 Eden Road, Lancaster, Pa.) and Noren Products (1010 O'Brien Drive, Menlo Park, Calif.). By using 2 mm diameter heat pipes, the device 10 can be manufactured having a total outer diameter of 5 mm, thereby allowing the device 10 to be used in laparoscopic applications.

The electrodes 12, 14 can be formed integral with the heat pipes 18, 20 such as by flattening the distal ends 29 of the pipes 18, 20. Alternatively, the electrodes 12, 14 can be formed separate from the heat pipes 18, 20 and then attached to the heat pipes 18, 20, such as by soldering.

Figure 2:
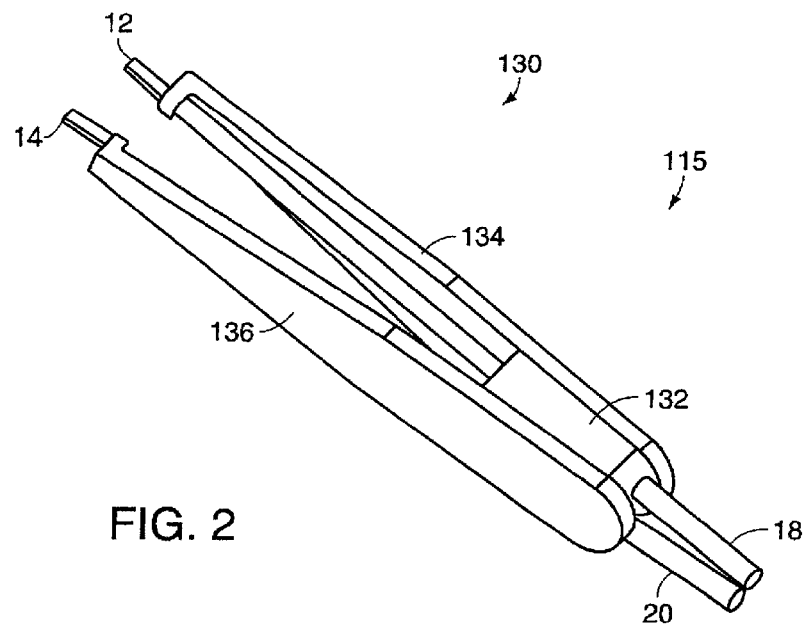
FIGS. 2 through 5 illustrate bipolar electrosurgical forceps.
Figure 3:
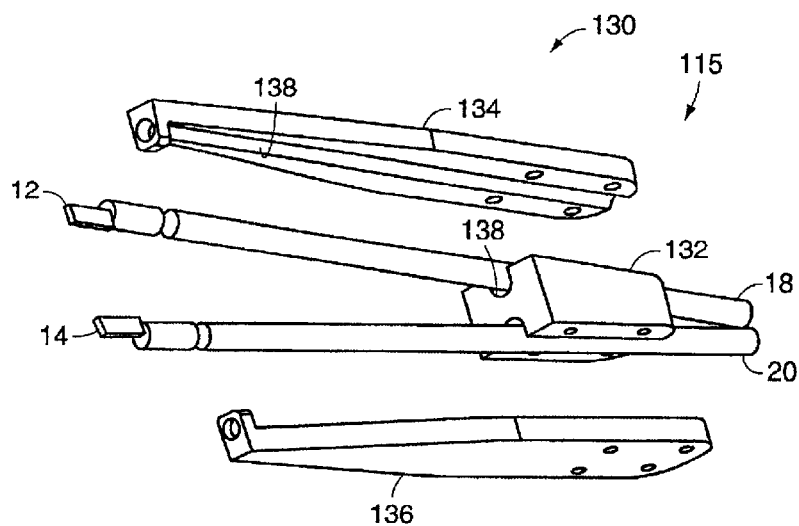

The principles of the bipolar electrosurgery device shown in FIG. 1 can be applied to surgical forceps. FIGS. 2–5 illustrate a bipolar electrosurgery device 115 formed as electrosurgery forceps 130. FIGS. 2 and 3 illustrate a device 130 having a first 18 and second 20 heat pipe that are secured within a connector or housing 132 and include cover members 134, 136. In one embodiment, the electrodes 12, 14 are integrally formed with the heat pipes 18, 20. Alternately, the electrodes 12, 14 of the device 130 are shaped and attached onto the distal ends of the heat pipes 18, 20. The electrodes 12, 14 can be removably attached such that the electrodes 12, 14 are disposable after use. The electrodes 12, 14 can also be permanently attached to the device 130, such as by soldering, for example, such that the entire device 130 can be sterilized or disposed after use. The cover members 134, 136 surround each heat pipe 18, 20 and provide grasping surfaces for a user. The cover members 134, 136 include recesses or grooves 138 that receive the geometry of the heat pipes 18, 20 and secure the heat pipes 18, 20 within the device 130. The connector 132 and the cover members 134, 136 act to electrically isolate the heat pipes 18, 20 and electrodes 12, 14 from each other and from a user. The connector 132 also includes recesses or grooves 138 for securing of the heat pipes 18, 20. The cover members 134, 136 attach to the connector 132 to secure the heat pipes 18, 20 within the connector 132.

As a user depresses the first cover member 134 and the second cover member 136 toward a central axis of the device 130, the first 18 and second 20 heat pipes elastically deform about the connector 132. A tissue can then be grasped between the electrodes 12, 14 of the forceps 130, thereby allowing for coagulation of the tissue. After coagulation is complete, a user releases the first 134 and second 136 cover members to release the tissue sample and allow the heat pipes 18, 20 to expand about the connector 132 to their original non-deformed positions.

Figure 4:
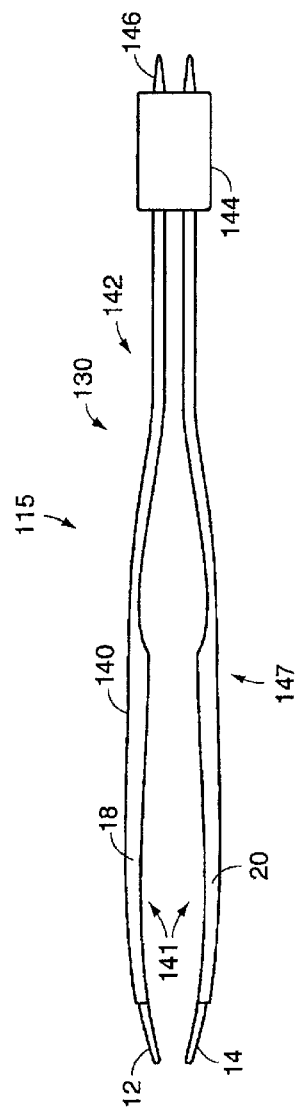
Figure 5:
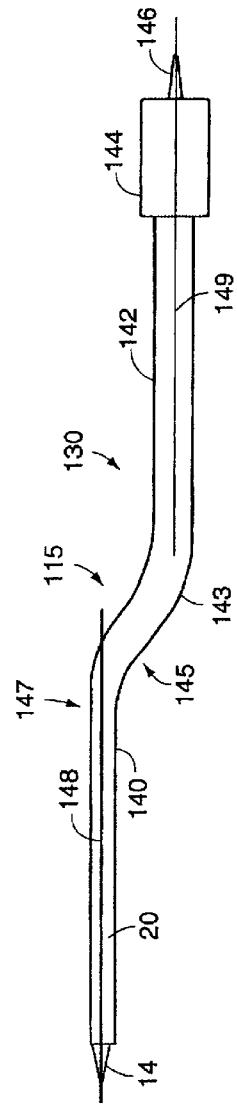

FIGS. 4 and 5 illustrate an alternative embodiment of the electrosurgery forceps 130. The forceps 130 include a first 12 and second 14 electrode coupled to a first heat pipe 18 and a second heat pipe 20, respectively. The electrodes 12, 14 can be attached to the heat pipes 18, 20 by soldering, for example, or the electrodes 12, 14 can be formed integrally with the heat pipes 18, 20. The heat pipes 18, 20 are covered with an insulation material 140 that acts as an electrical insulation for the forceps 130.

The heat pipes 18, 20 are attached to a pair of tines 142. A grasping portion 145 is located between the heat pipes 18, 20 and the tines 142. The grasping portion 145 can be held between a user's thumb and forefinger and allow the user to open and close the tines 142 of the forceps 130. The grasping portion 145 can include an offset 143, in one embodiment. The offset 143 allows the forceps 130 to be used at a surgical site while providing a clear view of the surgical site by a user. The heat pipes 18, 20 can attach to the offset 143 such that a long axis 148 of the heat pipe is parallel with a long axis 149 of the tines 142. The long axis 148 can also form an acute angle with the long axis 149.

The length of the heat pipes 18, 20 do not have to extend the entire length of the device 130. Preferably, the heat pipes 18, 20 have a length such that a proximal portion 147 of the heat pipes 18, 20 is approximately located at the offset 143 of the grasping portion 145. The heat pipes 18, 20 can also include a curvature 141 relative to a long axis of the heat pipes. The curvature 141 helps to align the electrodes 12, 14 during operation and ensures that the electrodes 12, 14 contact each other, during use, prior to the contacting of the tines 142.

Preferably, the tines 142 are formed of a titanium or stainless steel material. The tines 142 can also be covered with the insulating material 140 and include a housing 144 and a connector portion 146 to allow the electrosurgery forceps 130 to attach to a power source. By using the tines 142 rather than the heat pipes 18, 20 to compress the electrodes 12, 14 onto a tissue, fatigue stresses are not developed in the heat pipes 18, 20, thereby minimizing the risk of fatigue failure of the heat pipes 18, 20.

While the bipolar forceps described above include heat pipes and electrodes that are non-removably attached to or integrally formed with the instrument, the heat pipes and electrodes, in an alternate embodiment, can be removably attached to the forceps. The use of replaceable heat pipes or replaceable electrodes with the forceps allows different electrode geometries to be used with a single instrument. For example, the electrodes can have a narrow geometry, an angled geometry or a broad geometry. To prevent a user from requiring multiple bipolar devices at a surgical site, each with a particular electrode geometry, the use of removable heat pipes and electrodes allows many different electrode tips to be used during the course of a surgical procedure, without the need for multiple devices. FIG. 6 through FIG. 10 illustrate an embodiment of bipolar forceps having detachable heat pipes.

FIGS. 6 and 7 illustrate an embodiment of bipolar forceps, given generally as 200. The forceps 200 includes a first heat pipe 202 and a second heat pipe 204. The first heat pipe 202 includes a first electrode 212 and the second heat pipe 204 includes a second electrode 214. The device 200 includes a handle or tines 208 having a first arm 226 and a second arm 228 and having heat pipe mounts 206, one heat pipe mount 206 located on each arm 226, 228 of the handle 208. The handles 208 and heat pipe mount 206 can be formed of a stainless steel material or a titanium material. The handles 208 and heat pipe mount 206 can also be coated with an electrical insulator material. The heat pipes 202, 204 can slidably attach to the heat pipe mounts 206. The handle 208 also includes a connector 210 for connecting the electrodes 212, 214 to a voltage source. The handle 208 also includes a securing mechanism 216 that secures the heat pipes 202, 204 to the heat pipe mount 206 and prevents removal of the heat pipes 202, 204 from the device. Alternately, the device can include a securing mechanism that attaches the electrodes 212, 214 to the heat pipes 202, 204.

The heat pipe mounts 206 can also include a curvature relative to a long axis of the tines 208. Preferably, the heat pipes 202, 204 are formed of a material that is more compliant than the material that forms the heat pipe mounts 206. For example, the mounts 206 can be made from a stainless steel material while the heat pipes 202, 204 are formed of a copper material. During insertion, the heat pipes 202, 204 can deform to the curved shape of the mounts 206. Alternately, the heat pipes 202, 204 can include a curvature similar to the curved geometry of the mounts 206, thereby allowing the heat pipes 202, 204 to be inserted within the mounts 206, without deformation.

Figure 8:
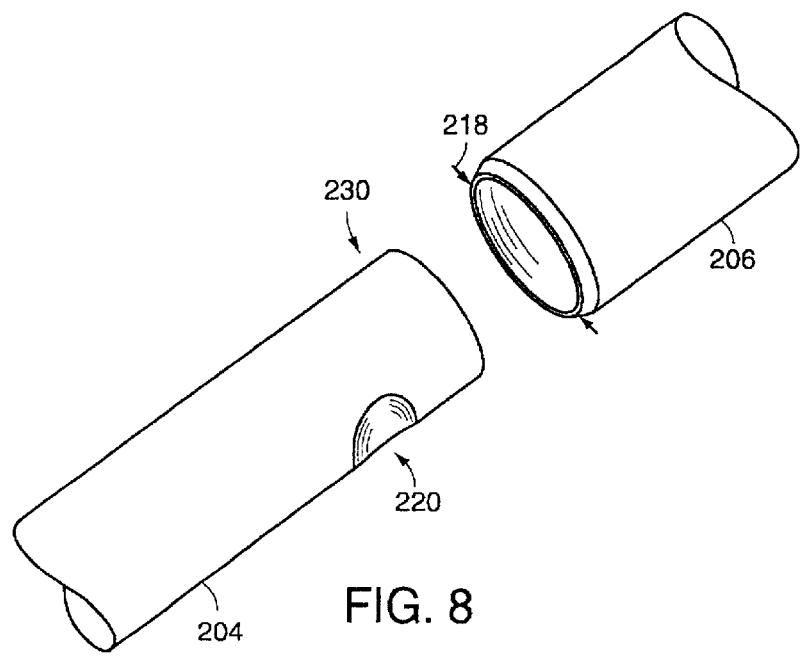
FIG. 8 illustrates the alignment of a heat pipe with a heat pipe mount of the bipolar surgical forceps.
Figure 9:
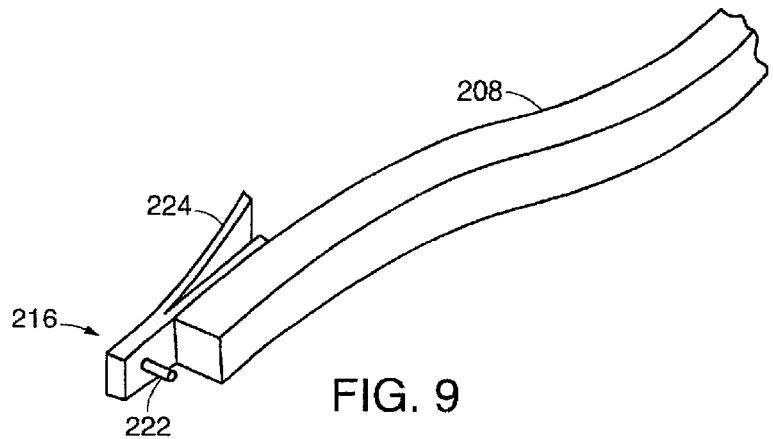
FIGS. 9 and 10 illustrate a heat pipe securing mechanism.

FIGS. 8 and 9 illustrate an example of a heat pipe securing mechanism 216. FIG. 8 illustrates a heat pipe 204 aligned with the heat pipe mount 206. The heat pipe mount 206 includes an inner diameter 218 such that the outer diameter of the heat pipe 204 fits within and is surrounded by the heat pipe mount 206 when positioned within the mount 206. The heat pipe 204 can include a proximal end 230 having a receptacle 220 that mates with the heat pipe securing mechanism 216 and secures the heat pipe 204 within the device 200. The receptacle 220 can be an indentation on the surface of the heat pipe 204.

FIG. 9 illustrates the heat pipe securing mechanism 216 mounted on the handle 208 of the device 200. The heat pipe securing mechanism 216 includes a pin 222, matable with the receptacle 220 of the heat pipe 204, and an actuator 224. After placing the heat pipe 204 within the heat pipe mount 206, a user depresses the actuator 224 of the heat pipe securing mechanism 216, thereby allowing positioning of the proximal end of the heat pipe 204 adjacent to the securing mechanism 216. In order to secure the heat pipe 204 to the device 200, the user aligns the receptacle 220 of the heat pipe with the pin 222 of the securing mechanism 216 and releases the actuator 224 to allow the pin 22 to engage the receptacle 220 of the heat pipe 204. Such engagement secures the heat pipe 204 and the electrode within the device 200.

Figure 10:
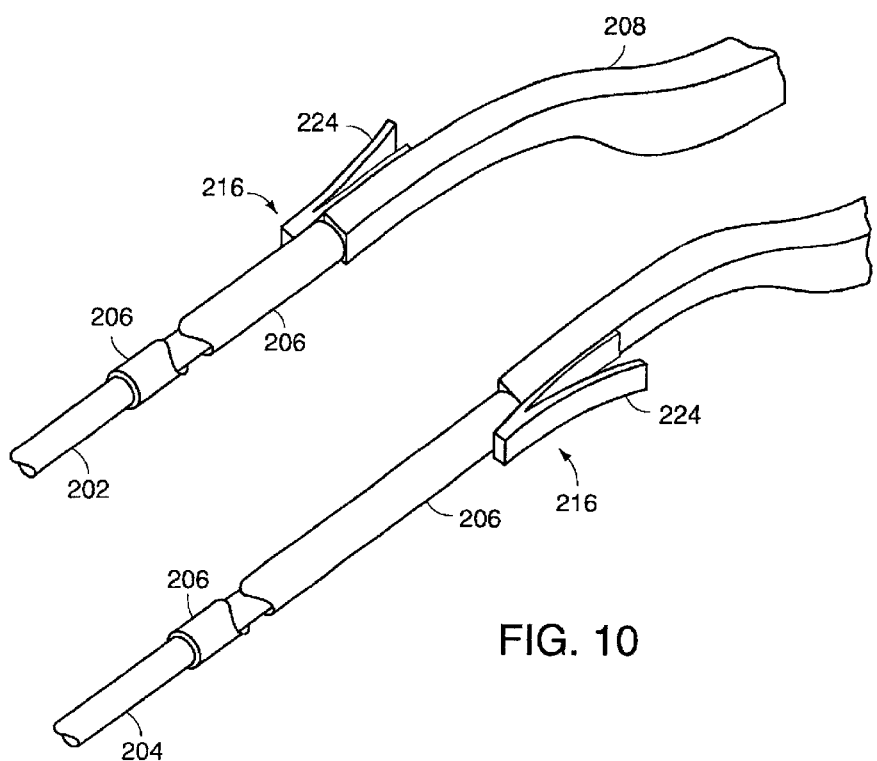

FIG. 10 illustrates the securing mechanism 216 in an engaged state. The heat pipes 202, 204 located within the heat pipe mounts 206 are engaged with the pins 222 of the heat pipe securing mechanisms 216.

While the embodiment of the securing mechanism 216 having a pin 222 and actuator 224 is shown, other types of securing mechanisms can be used. For example, a friction fit between the heat pipes 202, 204 and the heat pipe mount 206 can prevent the heat pipes from being removed from the device 200. Other types of securing mechanisms, such as thumb screws or magnets can also be used, for example. Also, while the above embodiments illustrate heat pipes 202, 204 removable from the electrosurgical device, the electrodes 212, 214 can, alternately, be removable from the heat pipes 202, 204.

While this invention has been particularly shown and described with references to preferred embodiments thereof, it will be understood by those skilled in the art that various changes in form and details may be made therein without departing from the scope of the invention encompassed by the appended claims.

What is claimed is:

1. Electrosurgery forceps comprising:
   an electrical connector;
   a pair of flexible tines extending from the connector;
   an electrode at the end of each tine; and
   a heat pipe within each tine, the heat pipe having a sealed internal cavity which contains a heat transfer fluid to dissipate heat from the electrode.

2. The forceps of claim 1 wherein the electrodes comprise a material having a thermal conductivity between 375 W/m¯K and 420 W/m¯K.

3. The forceps of claim 2 wherein the material comprises copper.

4. The forceps of claim 2 wherein the material comprises silver.

5. The forceps of claim 1 further comprising an insulating material surrounding an outer portion of the forceps.

6. The forceps of claim 1 wherein the heat pipes are removably attached to proximal tine portions.

7. The forceps of claim 6 further comprising heat pipe mounts attached to the proximal tine portions the heat pipes being slidably attached to the heat pipe mounts.

8. The forceps of claim 7 wherein the heat pipe mounts comprise a curved geometry relative to a long axis of the tines.

9. The forceps of claim 1 further comprising a securing mechanism that secures the heat pipes to the proximal tine portions.

10. The forceps of claim 1 wherein the tines comprise a grasping portion.

11. The forceps of claim 10 wherein the grasping portion comprises an offset that allows the forceps to be used at a surgical site while providing a clear view of the surgical site by a user.

12. The forceps of claim 11 wherein the heat pipe comprise a proximal portion, the proximal portion extending to the offset of the grasping portion.

13. The forceps of claim 1 wherein the electrodes are attached to the heat pipes.

14. The forceps of claim 1 wherein the electrodes are integrally formed with the heat pipes.

15. The forceps of claim 1 wherein the heat pipes comprise a curvature relative to a long axis of the heat pipes.

16. A method for applying energy to tissue comprising:
providing a bipolar electrosurgical forceps having a first electrode having a first polarity and a second electrode having a second polarity, a first time having a first heat pipe attached to the first electrode and a second tine having a second heat pipe attached to the second electrode, the heat pipes having a sealed internal cavity containing a heat transfer fluid for conducting heat from a surgical site;

attaching the forceps to a power source;

grasping tissue between the first electrode and the second electrode by compressing the tines; and driving energy from the first electrode to the second electrode.

17. The method of claim 16 further comprising allowing heat generated at the tissue to travel from the first electrode and the second electrode to the first heat pipe and the second heat pipe.

18. Bipolar electrosurgical forceps comprising:

first electrode means having a first polarity for providing energy to a tissue;

second electrode means having a second polarity for providing energy to the tissue;

means for compressing the first means and the second means onto the tissue; and heat pipe means for conducting heat from a surgical site, the heat pipe means for conducting having a sealed internal cavity which contains a heat transfer fluid.

19. Electrosurgery forceps comprising:

an electrical connector;

a pair of flexible tines each including a tine portion extending from the connector;

an electrode at the end of each tine;

a heat pipe removably attached to each tine portion to dissipate heat from the electrode; and heat pipe mounts attached to the tine portions, the heat pipes being slidably attached to the heat pipe mounts.

20. The forceps of claim 19 wherein the heat pipe mounts comprise a curved geometry relative to a long axis of the tines.

* * * * *